United States Patent
Heider et al.

[11] Patent Number: 6,066,759
[45] Date of Patent: May 23, 2000

[54] PROCESS AND DEVICE FOR PREPARING (CYCLO)ALIPHATIC BIURET GROUPS-CONTAINING POLYISOCYANATES

[75] Inventors: Wolfgang Heider, Neustadt; Stefan Wolff, Limburgerhof; Bernd Bruchmann, Ludwigshafen; Klaus Bittins, Frankenthal, all of Germany

[73] Assignee: BASF Aktiengesellschaft, Ludwigshafen, Germany

[21] Appl. No.: 08/981,636

[22] PCT Filed: Jul. 9, 1996

[86] PCT No.: PCT/EP96/03003

§ 371 Date: Mar. 9, 1998

§ 102(e) Date: Mar. 9, 1998

[87] PCT Pub. No.: WO97/03044

PCT Pub. Date: Jan. 30, 1997

[30] Foreign Application Priority Data

Jul. 12, 1995 [DE] Germany .................. 195 25 474

[51] Int. Cl.[7] .................................................. C07C 273/00
[52] U.S. Cl. ........................................ 560/335; 422/228
[58] Field of Search ............................ 560/335; 422/228

[56] References Cited

U.S. PATENT DOCUMENTS

| | | | |
|---|---|---|---|
| 3,285,705 | 11/1966 | Zuiderweg et al. | 422/228 |
| 3,358,010 | 12/1967 | Britain | 560/335 |
| 4,051,165 | 9/1977 | Wagner et al. | 560/335 |
| 4,374,093 | 2/1983 | Rollmann et al. | 422/228 |
| 4,438,074 | 3/1984 | Wilt | 422/228 |
| 4,613,686 | 9/1986 | Koenig et al. | 560/335 |
| 4,983,762 | 1/1991 | Robin | 560/335 |
| 5,102,630 | 4/1992 | Lee | 422/228 |
| 5,103,045 | 4/1992 | Robin et al. | 560/335 |
| 5,211,924 | 5/1993 | Lee et al. | 422/228 |

FOREIGN PATENT DOCUMENTS

| | | |
|---|---|---|
| 251 952 | 1/1988 | European Pat. Off. . |
| 259 233 | 3/1988 | European Pat. Off. . |
| 1543178 | 3/1965 | Germany . |
| 1931055 | 6/1969 | Germany . |
| 34 03 277 | 1/1984 | Germany . |

OTHER PUBLICATIONS

Kirk–Othmer, Reactor Technology, Encyclopedia of Chemical Technology, pp. 1040–1045, Sep. 10, 1993.

*Primary Examiner*—Gary Geist
*Assistant Examiner*—Taylor Victor Oh
*Attorney, Agent, or Firm*—Keil & Weinkauf

[57] ABSTRACT

In a process and an apparatus for preparing (cyclo)aliphatic polyisocyanates containing biuret groups from (cyclo) aliphatic diisocyanates and steam or a substance capable of splitting off water as reactants which are mixed with one another in a stirred reactor, the reactants are passes in countercurrent through a cascade-type stirred reactor comprising at least two stages. The dispersion of the gaseous reactant in the liquid reactant is reinforced by baffles installed in the stirred reactor. As baffles, use is made of discs provided with central openings and arranged at a distance from one another and/or strip baffles running in the longitudinal direction of the stirred reactor.

24 Claims, 3 Drawing Sheets

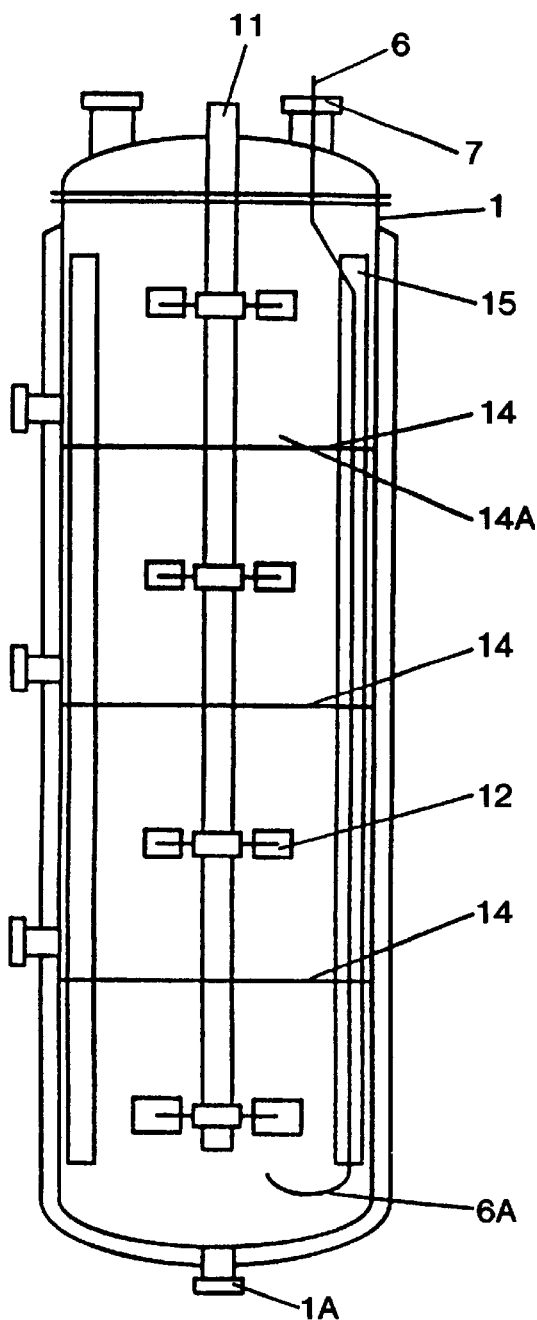
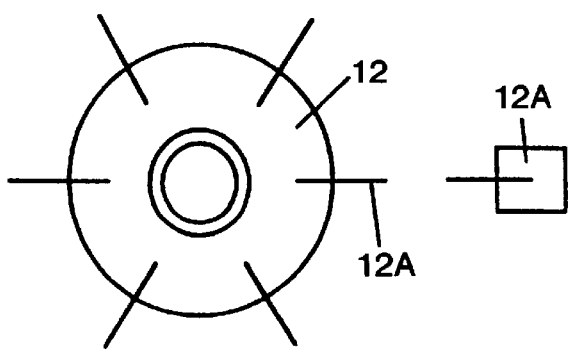
FIG. 3
FIG. 4

PROCESS AND DEVICE FOR PREPARING (CYCLO)ALIPHATIC BIURET GROUPS-CONTAINING POLYISOCYANATES

The invention relates to a process and an apparatus for preparing polyisocyanates containing biuret groups from cyclo(aliphatic diisocyanates using steam or a substance capable of splitting off water as reactants which are mixed with one another in a stirred reactor.

(Cyclo)aliphatic polyisocyanates containing biuret groups are used, inter alia, in high-quality light and weather-resistant, two-component PUR surface coatings. Other applications such as adhesives and dispersions are known. An overview of the literature is given in DE 34 03 277.

(Cyclo)aliphatic polyisocyanates containing biuret groups are prepared by reacting the diisocyanates with a certain amount of biuret-forming agent (water or a substance capable of splitting off water) at from 100 to 200° C. Subsequently, the excess monomeric diisocyanate is removed from the crude product thus formed by single-stage or multistage distillation. When t-BuOH (or another substance capable of splitting off water) is used as a biuret-forming agent, the urethane formed is catalytically dissociated into isobutene, carbon dioxide and an isocyanatoamine intermediate. However, this requires high reaction temperatures (>140° C.) and the reaction products take on a yellow discoloration. This is unfavorable since colorless products are required for application reasons, eg. in the case of a clear surface coating. In addition, the use of substances capable of splitting off water (eg. OH-containing molecules) as biuret-forming agents result in formation of by-products which do not have a biuret structure and impair the storage stability of the desired product or cause other process problems. Water is therefore preferred as biuret-forming agent. However, insoluble areas are generally formed during the reaction and the products obtained have a poor storage stability in terms of redissociation into the monomers. As a result, the limit value requiring statutory labeling of 0.5% of free monomeric diisocyanate is quickly exceeded, in particular on storage above room temperature. Proposals have been made for avoiding these disadvantages, (see, for example, EP 259 233 and EP 251 952). These documents describe the use of catalytic amounts of protic acids for avoiding by-product formation in the synthesis of aliphatic and cycloaliphatic polyisocyanates containing biuret groups.

Nevertheless, use of conventional stirred vessels does not succeed in completely reacting the water used as biuret-forming agent with the diisocyanate. Water vapor and diisocyanate escape together with the carbon dioxide formed in the reaction, in accordance with the existing partial pressure. This gas mixture condenses at cold places in the reactor and, in particular in the downstream off-gas cooler. There, the diisocyanate reacts with the water vapor to form polyureas which finally leads to blocking of the off-gas lines and the off-gas condensor. Reliable, long-term operation is not possible in this way.

It is an object of the present invention to provide a reaction procedure and an apparatus suitable for this purpose in which the escaping off-gas is virtually free of water vapor and therefore no measurable polyurea formation occurs in the off-gas system.

We have found that this object is achieved by the reactants being conveyed in countercurrent through a cascade-type stirred reactor comprising at least two stages. This effects a fine distribution of the steam introduced. The ring gas bubbles lose water vapor on their way through the isocyanate solution and become enriched in carbon dioxide.

The multistage nature of the cascade and the baffles installed in the stirred reactor, which baffles prevent the reactants from simply flowing straight through the stirred reactor, considerably increases the residence time of the gas bubbles in the liquid, so that complete absorption of the steam and thus complete reaction can be achieved.

According to a particularly advantageous embodiment of the process of the present invention, the distribution of the gaseous material in the liquid reactant is improved by baffles installed in the stirred reactor. The baffles which can be used are disks provided with central openings and arranged at a distance from one another. In addition, strip baffles running in the longitudinal direction of the stirred reactor can be used. From 10 to 95% by volume of nitrogen and/or carbon dioxide can be mixed into the reactant used as biuret-forming agent, preferably steam. The reaction is carried out at from 60 to 200° C., preferably from 100 to 150° C. The off-gas flowing from the top end of the stirred reactor is preferably scrubbed with cold (cyclo)aliphatic diisocyanate which is subsequently fed to the process. If the off-gas formed in the reaction is conveyed via an off-gas condensor which is additionally flushed with cold diisocyanate, no polyurea residues can be detected in the off-gas system even when the process has been running for a long time.

For carrying out the process, the invention provides a stirred reactor which comprises an upright tubular vessel in which there is fixed, parallel to the longitudinal axis and able to rotate, a drive shaft to which are fixed at least two disk stirrers at a distance from one another, where between these disk stirrers there are arranged disk baffles fixed to the inner wall of the vessel and having a central opening. It has been found that, depending on the reaction parameters, it is advantageous to use from 2 to 6 disk stirrers and from 1 to 5 disk baffles. The ratio of the opening of the disk baffles to their total area is derived from the stirrer size.

According to one embodiment of the stirred reactor of the present invention, the inner wall of the reactor can be provided with strip baffles running parallel to the longitudinal axis of the reactor and extending radially inwards. These can preferably be fixed so as to leave a gap between the baffle and the inner wall of the reactor. Advantageously, at least 4 strip baffles equally spaced around the reactor wall are provided. The strip baffles are standardized, their width being 0.1 D, where D is the diameter of the vessel.

The stirred reactor can be surrounded by a heatable jacket. Advantageously, the top end of the stirred reactor is connected to a cooling vessel in the lower part of which a cooler is installed. Above this cooler there is located an injector for the liquid reactant. This unit opens into an off-gas line. Advantageously, the ratio of the height of the stirred reactor to its diameter is in the range from 2 to 6 and is preferably greater than 4.5.

Reactors of the above-described construction enable the process of the present invention to be carried out particularly advantageously.

Further details and advantages of the invention can be taken from the description of the experimental plant shown in the drawing. In the figures:

FIG. 3 shows an enlarged section of the stirred reactor of the present invention, FIG. 4 shows a plan view of a disc stirrer arranged in the stirred reactor.

Figure 1:
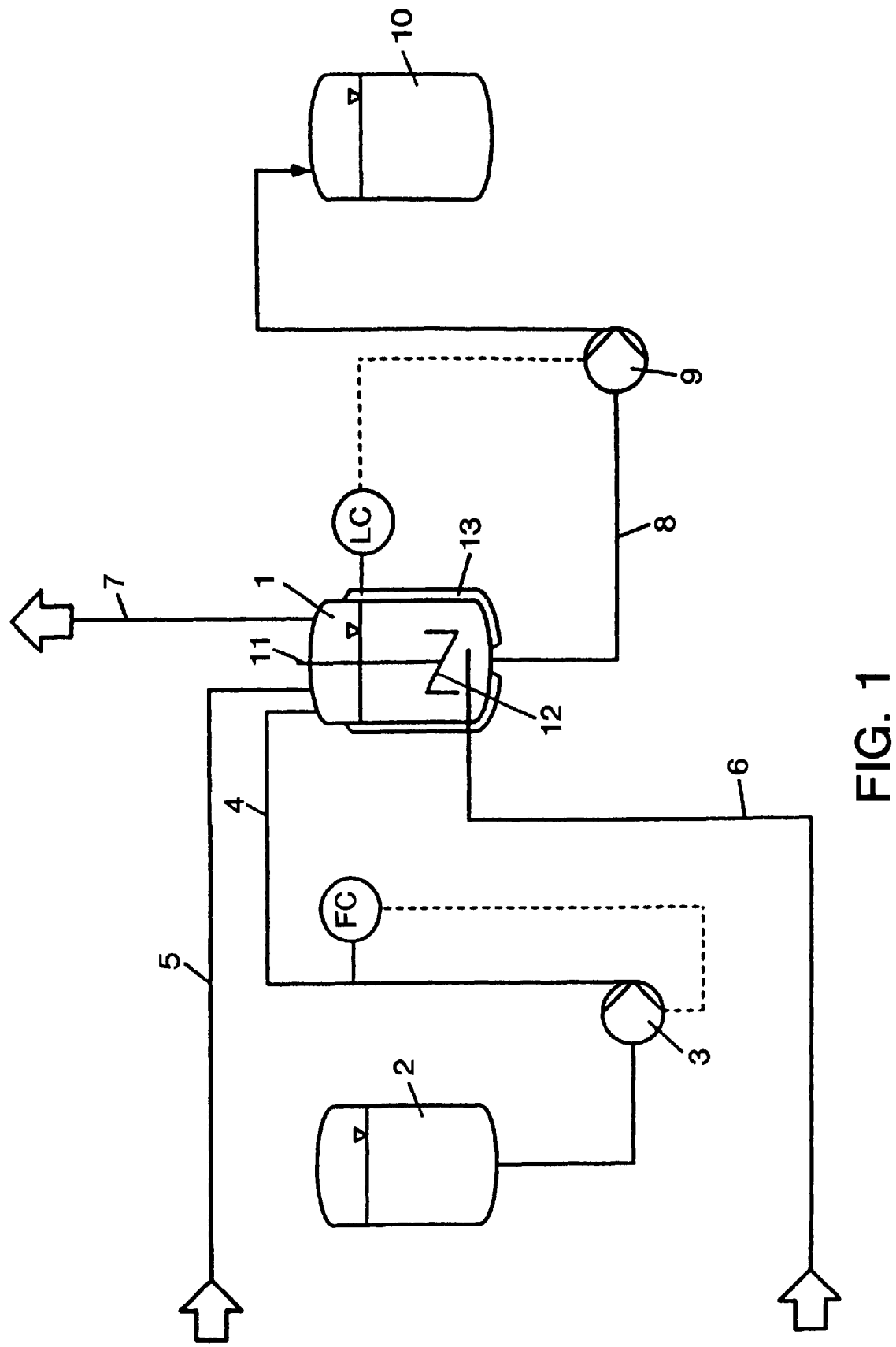
FIG. 1 shows a known plant comprising a simple stirred vessel.

In the known plant shown in FIG. 1, the reaction for preparing (cyclo)aliphatic polyisocyanates containing biuret groups is carried out in a simple stirred reactor 1. Hexamethylene diisocyanate (HDI) as one of the two reactants is fed from a vessel 2 via a pump 3 through a line 4 to the reactor from above. Catalysts, for example, strong inorganic Lewis or Brenstedt acids (cf. DE-A-15 43 178) and/or salts of nitrogenous bases and inorganic and/or organic acids (cf. DE-A-19 31 055) can be introduced through line 5. In the experimental plant, di-2-ethylhexyl phosphate was used as catalyst. As second reactant, steam diluted with gaseous nitrogen was introduced through line 6 into the lower part of the stirred reactor. The off-gases formed in the reaction, in particular $CO_2$, are conducted away from the top of the stirred vessel 1 through the line 7. The product formed in the reaction, namely the polyisocyanate containing biuretic groups is taken from the lower end of the vessel 1 through line 8 and conveyed via the pump 9 to a receiver 10. In the stirred vessel 1 there is arranged a disk stirrer 12 rotatable about a vertical shaft 11. The temperature is the stirred vessel 1 is adjusted by means of a heatable jacket 13 surrounding the vessel.

Figure 2:
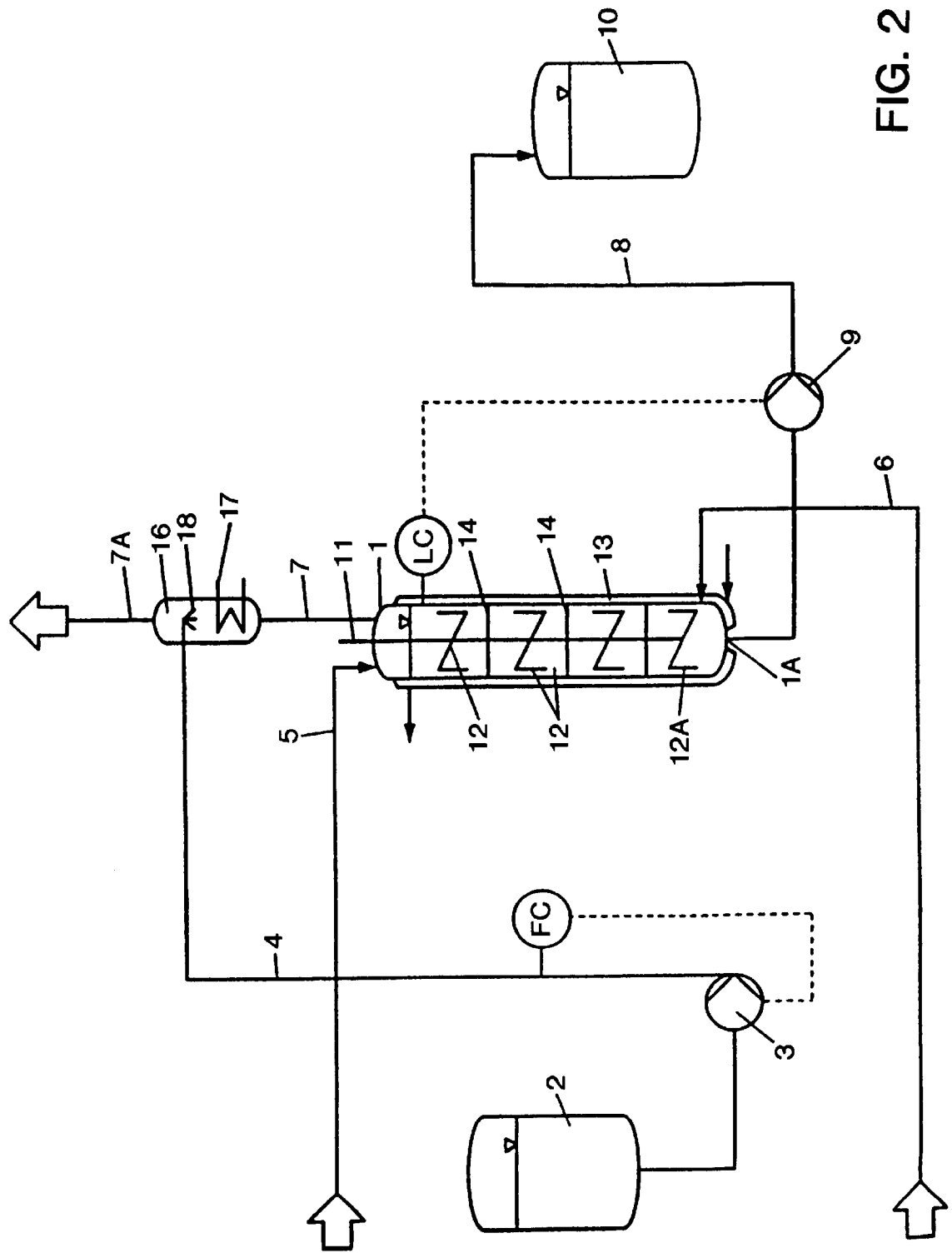
FIG. 2 shows a plant according to the present invention comprising a cascade-type stirred reactor.

In the plant according to the present invention shown in FIG. 2, the stirred vessel, here likewise denoted by 1, has a cascade-type construction, as is shown in detail in FIG. 3. In this vessel four disk stirrers 12 are arranged at intervals along the rotating shaft 11 running parallel to the longitudinal axis of the vessel 1. Between the disk stirrers 12 there are located three disk baffles 14 which are fixed to the wall of the stirred vessel 1 and have a circular central opening. In the embodiment shown in FIG. 3, the stirred vessel 1 has an internal diameter of 100 mm. The opening of the disk baffles 14 has a diameter of 52 mm. The disk stirrers 12, of which one is shown in FIG. 4, can have different dimensions. In general, standard disk stirrers are used. In the present case, the disk of the bottom disk stirrer 12 has a diameter of 37.5 mm. The external diameter including the vertical stirring surfaces 12A is 50 mm. The stirring surfaces 12A have a rectangular shape with a height of 10 mm and a width of 12.5 mm. The other three disk stirrers 12 have an internal diameter of 30 mm and an external diameter of 40 mm, with the dimensions of the disks being 8×10 mm. In the interior of the stirred vessel 1 there are arranged four strip baffles 15 parallel to the longitudinal axis of the stirred vessel spaced at 90° from one another with a spacing from the wall of 1 mm. The rotating shaft 11 together with the disk stirrers 12 attached thereto rotates at from 500 to 900 revolutions per minute.

In the plant according to the present invention shown in FIG. 2, the reactant HDI is also fed to the stirred vessel 1 from the vessel by means of the pump 3 through the line 4. The line 4 here leads via an injector 18 into a cooling vessel 16 fitted with a cooler 17. The off-gas flowing from the stirred vessel 1 through line 7A is cooled by means of this cooler. Deposition of residues is thereby prevented. From the upper part of the cooling vessel 16, the off-gas consisting essentially of $CO_2$ flows away through line 7A. The steam/nitrogen mixture flowing in through line 6 is fed in at the lower end of the stirred vessel 1. In the embodiment shown in FIG. 3, the line 6 enters at the upper end of the stirred vessel but the steam flows out at the lower end of the stirred vessel 1 at 6A. The product is taken from the lower end of the stirred vessel 1 at 1A and is conveyed by means of the pump 9 vial the line 8 to the receiver 10.

Both the known plant shown in FIG. 1 and the plant according to the present invention shown in FIG. 2 were operated continuously and semicontinuously. In the semicontinuous procedure, HDI and catalyst are initially charged and heated. Subsequently, the mixture of steam and nitrogen is introduced continuously, the reaction taking a total of about 3–4 hours. In the through-flow procedure, HDI and catalyst are continuously metered into the reactor 1 and the mixture of steam and nitrogen is introduced in parallel thereto. The crude product of HDI-biuret oligomers and excess monomers is continuously discharged to the vessel 10. The crude product is subsequently worked up by means of distillation.

Continuous and batchwise experiments were carried out using the abovedescribed plants comprising a simple stirred vessel (FIG. 1) and cascade-type stirred vessel (FIG. 2). It has been found that the conversion of the water used is significantly higher in the cascade=type stirred vessel both in the continuous and the batchwise process. This can be seen in the difference between the "actual NCO value" and the "ideal NCO value" of the crude product, which are shown in Tables 1 and 2 below. The "ideal NCO value" can be calculated using the assumption the 1 mol of water reacts with exactly 3 mol of NCO groups. If the actual conversion is lower than the ideal conversion, ie. the NCO value is higher (pure HDI has 50% of NCO), then not all the water could have reacted and the reactor used does not have optimum efficiency. An NCO value lower than the "ideal NCO value" means that additional side reactions have taken place.

The experiments carried out using the cascaded stirred vessel of the present invention and a simple stirred vessel have given the results shown in the tables below.

TABLE 1

Semicontinuous process

| Reaction conditions | Semicontinuous | |
|---|---|---|
| | cascaded stirred vessel | simple stirred vessel |
| Amount of water, g | 24.05 | 9.00 |
| Amount of HDI, g | 2230.00 | 600.00 |
| NCO value (actual) | 42.70% | 40.70% |
| NCO value (ideal, 3 mol of NCO/mol of $H_2O$) | 43.10% | 40.37% |
| Steam introduction | about 50 minutes | about 50 minutes |
| Total residence time | 3 to 4 hours | 3 to 4 hours |
| Cat. (di-2-ethylhexyl phosphate), mol% based on HDI | 0.20% | 0.20% |
| Temperature, °C. | 130.00 | 130.00 |
| Operating Pressure | atmospheric | atmospheric |

TABLE 2

Continuous process

| Reaction conditions | Continuous | |
|---|---|---|
| | cascaded stirred vessel | simple stirred vessel |
| Amount of water, g/h | 10.02 | 9.48 |
| Amount of HDI, g/h | 1000.00 | 1000.00 |
| NCO value (actual) | 43.50% | 44.73% |
| NCO value (ideal, 3 mol of NCO/mol of $H_2O$) | 43.60% | 43.97% |
| Residence time | 3 hours | 1 hour |
| Cat. (di-2-ethylhexyl phosphate), mol% based on HDI | 0.20% | 0.20% |
| Temperature, °C. | 130.00 | 130.00 |
| Operating Pressure | atmospheric | atmospheric |

Overall, the experimental results show that the process of the present invention using the novel apparatus provided for this purpose leads to significantly better results than the known processes carried out using a simple stirred vessel.

We claim:

1. A process for preparing (cyclo)aliphatic polyisocyanates containing biuret groups from (cyclo)aliphatic diisocyanates and steam or a substance capable of splitting off water as reactants which are mixed in a reactor arrangement, which process comprises conveying the reactants in countercurrent through a stirred reactor comprising at least two stirring means arranged at a distance from one another at different levels of the reactor to form a cascade of stirring means.

2. The process defined in claim 1, wherein the stirred reactor further comprises baffles installed between the stirring means.

3. The process defined in claim 2, wherein the baffles are in the form of disks having central openings and said discs being arranged at a distance from one another.

4. The process defined in claim 2, wherein the baffles are in the form of strip baffles which are arranged in the longitudinal direction of the stirred reactor.

5. The process defined in claim 18, wherein the steam comprises from 10 to 95% by volume of nitrogen and/or carbon dioxide.

6. The process defined in claim 1, wherein the reaction temperature is from 60 to 200° C.

7. The process defined in claim 1, wherein the off-gas flowing from the top end of the stirred reactor is scrubbed with cold (cyclo)aliphatic diisocyanate which is subsequently fed to the process.

8. An apparatus for carrying out the processss defined in claim 1, wherein the stirred reactor (1) which comprises an upright tubular vessel in which there is fixed, parallel to the longitudinal axis and able to rotate, a drive shaft (11) to which are fixed at least two disk stirrers (12) at a distance from one another, where between these disk stirrers (12) there are arranged disk baffles (14) fixed to the inner wall of the vessel (1) and having a central opening (14A).

9. The apparatus defined in claim 8, provided with 2 to 6 disk stirrers (12) and from 1 to 5 disk baffles (14).

10. The apparatus defined in claim 8, wherein the inner wall of the stirred reactor (1) comprises strip baffles (15) arranged parallel to the longitudinal axis of the reactor and extending radially inwards.

11. The apparatus defined in claim 10, wherein the strip baffles (15) are fixed so as to leave a gap between the baffle and the inner wall of the reactor (1).

12. The apparatus define in claim 10, comprising at least four strip baffles (15) equally spaced apart around the reactor wall.

13. The apparatus defined in claim 8, wherein the stirred reactor (1) is surrounded by a heatable jacket (13).

14. The apparatus defined in claim 8, further comprising a cooling vessel (16) connected to the top of the upright tubular vessel of the stirred reactor (1), which cooling vessel (16) comprises a cooler (17), an injector (18) which is arranged above the cooler (17), and an off-gas line (7A) which is arranged above the injector.

15. The apparatus defined in claim 8, wherein the ratio of the height of the stirred reactor to the diameter thereof is greater than 2.

16. The process defined in claim 1, wherein the reaction temperature is from 100 to 150° C.

17. The apparatus defined in claim 8, wherein the ratio of the height of the stirred reactor to the diameter thereof is greater than 4.5.

18. A process for preparing (cyclo)aliphatic polyisocyanates containing biuret groups from (cyclo)aliphatic diisocyanates and steam as reactants which are mixed in a reactor arrangement, which process comprises conveying the reactants in countercurrent through a stirred reactor comprising at least two stirring means arranged at a distance from one another at different levels of the reactor to form a cascade of stirring means.

19. The process defined in claim 18, wherein the stirred reactor further comprises baffles installed between the stirring means.

20. The process defined in claim 19, wherein the baffles are in the form of disks having central openings and said discs being arranged at a distance from one another.

21. The process defined in claim 19, wherein the baffles are in the form of strip baffles which are arranged in the longitudinal direction of the stirred reactor.

22. The process defined in claim 18, wherein the reaction temperature is from 60 to 200° C.

23. The process defined in claim 18, wherein the reaction temperature is from 100 to 150° C.

24. The process defined in claim 18, wherein the off-gas flowing from the top end of the stirred reactor is scrubbed with cold (cyclo)aliphatic diisocyanate which is subsequently fed to the process.

* * * * *